United States Patent [19]

Ono et al.

[11] 3,975,570

[45] Aug. 17, 1976

[54] ADHESIVE TAPES HAVING A PRESSURE SENSITIVE ADHESIVE COMPOSITION CONTAINING HYDROXYETHYL CELLULOSE

[75] Inventors: Tomoyoshi Ono, Hino; Yoshihiko Matsuguma, Hachioji, both of Japan

[73] Assignee: Teijin Limited, Japan

[22] Filed: June 27, 1975

[21] Appl. No.: 590,923

Related U.S. Application Data

[62] Division of Ser. No. 419,068, Nov. 26, 1973, Pat. No. 3,928,262.

[30] Foreign Application Priority Data

Dec. 21, 1972  Japan.............................. 47-127626

[52] U.S. Cl................................. 428/355; 260/17 R; 428/535
[51] Int. Cl.$^2$...................... B32B 23/08; C08L 1/26
[58] Field of Search................... 428/355, 500, 535; 260/17 R

[56] References Cited

UNITED STATES PATENTS

| | | | |
|---|---|---|---|
| 3,446,767 | 5/1969 | Nolan.............................. | 260/17 R |
| 3,535,295 | 10/1970 | Davis.............................. | 260/80.8 |
| 3,713,872 | 1/1973 | Porter et al...................... | 260/17 R |
| 3,740,367 | 6/1973 | Winkelblech..................... | 260/17 R |
| 3,764,587 | 10/1973 | Zunker............................ | 260/17 R |
| 3,806,464 | 4/1974 | Matrick et al. .................. | 260/17 R |

*Primary Examiner*—Marion E. McCamish
*Assistant Examiner*—R. J. Roche
*Attorney, Agent, or Firm*—Sherman & Shalloway

[57] ABSTRACT

An adhesive composition comprising, of the total composition of 100 parts by weight, 90–99 parts by weight on a tacky copolymer of an alkyl acrylate, the alkyl group of which contains 1 to 14 carbon atoms and the average number of which carbon atoms is 4 to 12, with a compound having a double bond and copolymerizable therewith, and 10–1 parts by weight of a hydroxyethyl cellulose.

2 Claims, No Drawings

ADHESIVE TAPES HAVING A PRESSURE SENSITIVE ADHESIVE COMPOSITION CONTAINING HYDROXYETHYL CELLULOSE

This is a division of application Ser. No. 419,068 filed Nov. 26, 1973, now U.S. Pat. No. 3,928,262.

This invention relates to adhesive compositions. More particularly, the invention relates to pressure-sensitive adhesive compositions suitably used for the preparation of adhesive tapes, adhesive sheet materials or the like, which possess excellent adhesiveness when adhered to an object and, in addition, does not impede the breathing activity of the object to which application has been made.

The adhesive tapes obtained by coating a plastic film, cloth or nonwoven fabric with a pressure-sensitive adhesive composition are also used in the medical field as, say, surgical tapes. In the case of an adhesive tape used in the medical field, it is important that it possesses breathability so as not to hinder the ventilation of bodily parts, say, the skin to which it has been applied.

For providing an adhesive tape or sheet material with breathability, a proposal has been made of perforating the conventional adhesive tapes or sheet materials not possessing moisture or gas permeability with numerous minute holes, and various methods of accomplishing this have been suggested. However, the moisture or gas permeability is limited to only the perforated portions in the case of the adhesive tapes obtained by these suggested methods, and those portions where the adhesive is present is essentially nonpermeable. Thus, these tapes cannot possibly be considered as being breathable, and the effects obtained by their use are not fully satisfactory. Further, these methods are not economically advantageous, since there is usually required the extra step of perforation, in addition to the step of manufacturing the adhesive tape.

Again, there has also been proposed a method of preparing a breathable adhesive tape or sheet material by coating a porous backing with the usual nonpermeable adhesive in a noncontinuous fashion such as lineally or spottily. However, in the case of an adhesive tape having a non-continuous adhesive layer or this king, there is the drawback that since the area of adhesion becomes small, inadequancy of adhesive strength is brought about. Another shortcoming is that the breathing activity is impeded at the portions where the adhesive is present, since the adhesive itself is inherently nonpermeable.

As another method there is one which proposes the use of a volatile solvent-containing adhesive in preparing the adhesive tape, the solvent being removed from the adhesive layer by volatilization to impart porosity to the adhesive layer. While this method can be regarded as excelling the previous two methods in that this method imparts breathability to the adhesive layer also, there is the disadvantage that complicated steps are required in that the adhesive solution is first applied to a liner having a flat strippable surface, after which it is brought to a semi-dried state, then transferred to a porous backing with pressure, and thereafter dried completely.

Further, since in all of these methods holes are formed in the adhesive layer as well as the backing, there is the possibility when these adhesive tapes are used with skin injuries that impurities from the outside might reach the wound and cause its infection.

It is therefore an object of the present invention to provide an adhesive composition in which the continuous layer of a pressure-sensitive adhesive per se possesses breathability.

Another object of the invention is to provide a pressure-sensitive adhesive tape in which the per se breathable continuous layer of a pressure-sensitive adhesive composition is adhered to a gas- and moisture-transmissible sheet substrate.

In consequence of our extensive researches with a view to achieving the foregoing objects, we found that by incorporating a small amount of a hydroxyethyl cellulose in a copolymer consisting predominantly of an alkyl acrylate an adhesive composition excelling in breathability could be obtained without impairment of hardly any of the adhesive properties of the adhesive layer. Thus, the present invention was perfected.

Thus, an adhesive composition is provided by the present invention in which, of the 100 parts by weight of the total composition, the major components consist of 90 – 99 parts by weight of a tacky copolymer of an alkyl acrylate whose alkyl group contains 1 to 14 carbon atoms, the average number of which carbon atoms is 4 to 12, with a compound having a double bond and copolymerizable therewith, and 10 – 1 parts by weight of a hydroxyethyl cellulose.

The use as a pressure-sensitive adhesive of the copolymers consisting predominantly of an alkyl acrylate has been known hitherto, and it is known that these copolymers are superior with respect to their adhesiveness, weatherability and nontoxicity. The pressure-sensitive sheet materials and tapes obtained by coating plastic films, cloths and nonwoven fabrics with these copolymers are used for medical purposes. In addition, they are used for such purposes as materials for making stationery items, electrical insulation material and industrial materials. However, these copolymers per se do not possess breathability.

A novel aspect of the present invention resides in the fact that breathability is imparted to the pressure-sensitive adhesive by the incorporation of 10 – 1 parts by weight of a hydroxyethyl cellulose per 100 parts by weight of the total composition.

While the reason why the invention adhesive composition possesses breathability is not entirely clear, it is believed that it is due to the fact that moisture is diffusible via the hydroxyethyl cellulose portion that has been uniformly dispersed in the alkyl polyacrylate copolymer. According to our investigations, even though additions are made of the other compounds similar to hydroxyethyl cellulose, e.g., hydroxypropyl cellulose, carboxymethyl cellulose and sodium polyacrylate, conspicuous results, as in the case where a hydroxyethyl cellulose was added, could hardly be noted. The reason therefor is believed to be due to the fact that because of the lack of hydrophilicity the diffusion of moisture does not take place adequately or the uniform dispersion of the additive throughout the alkyl polyacrylate copolymer does not take place.

When the content of the hydroxyethyl cellulose exceeds 10% by weight of the total composition in this case, the adhesive properties, and especially the adhesive force, of the adhesive composition decline. On the other hand, when the content of the hydroxyethyl cellulose is less than 1% by weight, not much improvement can be noted in the breathability of the composition. In either case, this is undesirable, since the resulting product is inadequate for use as a breathable adhesive composition. Thus, the content of the hydroxyethyl cellulose should preferably be in the range of 3 – 7% by weight of the composition.

The hydroxyethyl cellulose used in this invention as the additive is readily available as a commercial product (e.g., NATROSOL, a product of Hercules Incorporated, U.S.A.), and it is conveniently used as an aqueous solution of 1 – 5% by weight concentration.

As the alkyl group of the alkyl acrylate of the copolymer used for adhesive component in this invention, said group containing 1 to 14 carbon atoms can be used, and the average number of the carbon atoms of the alkyl group must be at least 4.

By the expression "average number of the carbon atoms of the alkyl group" is meant a value defined by the following equation.

$$\text{Average number of the carbon atoms of the alkyl group} = \frac{\Sigma [n \times (\text{the moles of alkyl acrylates having } n \text{ carbon atoms in the alkyl groups})]}{(\text{total moles of the alkyl acrylates})}$$

Alkyl acrylates in which the alkyl group has at least 4 carbon atoms are preferred. Examples of these alkyl acrylates are butyl acrylate, amyl acrylate, hexyl acrylate, heptyl acrylate, octyl acrylate, nonyl acrylate, decyl acrylate and 2-ethylhexyl acrylate, the 2-ethylhexyl acrylate being especially preferred for its good ability of imparting adhesiveness and also from the commercial standpoint. The acrylic acid esters having lower alkyl groups of less than 4 carbon atoms such as methyl acrylate and ethyl acrylate may also be used by mixing in like manner, provided that the average number of the carbon atoms in the whole of the alkyl acrylates used is at least 4. When the average number of the carbon atoms of the alkyl group is less than 4, this is undesirable, since the resulting copolymer lacks tackiness.

As the monomer to be copolymerized with the aforesaid alkyl acrylates, any monomer that is copolymerizable with the alkyl acrylates will do. Particularly preferred are, however, the polar monomers such as acrylic acid and methacrylic acid; the polyfunctional compounds having at least two nonconjugated carbon-to-carbon double bonds in their molecular structure such as diallyl phthalate, ethylene glycol dimethacrylate, polyethylene glycol dimethacrylate, trimethylolethane trimethacrylate and pentaerythritol methacrylate; vinyl acetate, methyl methacrylate and maleic anhydride.

The polyalkyl acrylates are deficien in their internal cohesive strength and tend to cause cohesive failure of the adhesive layer when used for the preparation of pressure-sensitive adhesive tapes. In this case, when a polar monomer such as acrylic or methacrylic acid is used in a small amount as the monomer to be copolymerized with the alkyl acrylates, the resulting copolymer does not exhibit cohesive failure and is effectively used as the pressure-sensitive adhesive component.

The copolymerization of methyl methacrylate and/or vinyl acetate along with the foregoing polar monomers is also a preferred mode of operation. The methyl methacrylate and/or vinyl acetate is used in an amount of preferably one mole per 5 moles or more of the acrylic acid esters and such a rate that the total of the alkyl acrylate, methyl methacrylate and/or vinyl acetate accounts for 75 – 95 moles while the acrylic acid and/or methacrylic acid accounts for 5 – 25 moles. Thus, the internal cohesive strength of the copolymer can be further enhanced.

A copolymer obtained by copolymerizing along with the methyl methacrylate and/or vinyl acetate and the polar monomers such as acrylic or methacrylic acid 0.002 – 0.05 mol% of the total composition of a polyfunctional compound, such as mentioned above, is also a very excellent copolymer. In this case the use of polyethylene glycol dimethacrylate is especially suitable.

The copolymer consisting predominantly of an alkyl acrylate can be readily prepared by the so-called solution polymerization method, i.e., by dissolving the aforementioned alkyl acrylate in a suitble solvent along with a monomer that is copolymerizable therewith followed by the addition of a catalyst and heating. It can also be prepared by other polymerization methods, say, the emulsion polymerization method.

As the catalyst to be used in the solution polymerization method, the radical initiators such, for example, as benzoyl peroxide, azobisisobutyronitrile and lauryl peroxide are useful. These are usually used in an amount of 0.2 – 2.0% by weight based on the total amount of the monomer. On the other hand, usable as the solvent are, for example, the esters such as methyl acetate and ethyl acetate, the aromatic hydrocarbons such as benzene, toluene and xylene, the alicyclic hydrocarbons such as cyclohexane, the halogenated hydrocarbons such as methylene chloride and ethylene dichloride, and the ketones such as acetone and methyl ethyl ketone. Of these, preferred is ethyl acetate in view of its possession of an especially suitable boiling point and the fact that the solubility of the resulting copolymer is good. A monomer concentration at the time of the polymerization reaction of 35 – 60% by weight is preferred. When the monomer concentration at the time of the polymerization reaction is less than 35% by weight, the polymerization speed becomes extremely slow, whereas if this concentration exceeds 60% by weight, the evolution of polymerization heat becomes great. Usually, with a polymerization temperature of 50° – 70°C. and a polymerization time of 5 – 10 hours the copolymer can be obtained at a polymerization conversion of above 95%.

On the other hand, when the emulsion polymerization method is employed, the monomers are usually emulsified in water and polymerized in the presence of a water-soluble polymerization initiator. The amount of water usually used in this case is preferably 0.5 – 3 times the total weight of the monomers. Usable as the emulsifiers are the usual emulsifiers such as sodium alkylaryl polyester sulfonates and sodium alkylarylsulfonates, while as the polymerization initiators usable are the usual water-soluble polymerization initiators such as potassium persulfate and ammonium persulfate. If in this case conjoint use is made of a reducing agent such as sodium hydrogen sulfite, the polymerization reaction can be carried out at a lower temperature and more promptly. While the polymerization conditions will vary depending upon such as the class of monomers used, the copolymer is usually readily obtained with a temperature of 20° – 70°C. and a polymerization time of 1 – 10 hours.

The so obtained copolymer consisting predominantly of an alkyl acrylate is usually used as a solution in the esters such as methyl acetate and ethyl acetate, the aromatic hydrocarbons such as benzene, toluene and xylene, the alicyclic hydrocarbons such as cyclohexane, and the halogenated hydrocarbons such as methylene chloride and ethylene chloride. The foregoing organic solvent solution of a copolymer consisting predominantly of an alkyl acrylate is desirably used after adjusting its solids content to 5 – 25% by weight, and preferably 10 – 15% by weight.

The adhesive composition according to the present invention is prepared, for instance, in the following manner. The organic solvent solution of a copolymer consisting predominantly of an alkyl acrylate is mixed with an aqueous hydroxyethyl cellulose solution with well stirring to prepare a homogeneous dispersion. When this mixture is directly applied to a suitable backing in customary manner and dried, a pressure-sensitive adhesive tape or sheet material having an adhesive layer consisting of a breathable adhesive composition can be prepared. Alternately, if the foregoing mixture is applied uniformly to a flat, smooth liner having a strippable surface, a breathable adhesive composition film is obtained. When the so obtained film is then transferred with pressure to a suitable backing, a breathable adhesive tape or sheet material can be prepared.

It is an advantage from the operational standpoint to use as the organic solvent solution of a copolymer consisting predominantly of an alkyl acrylate one whose solids concentration is 5 – 25% by weight, and preferably 10 – 15% by weight.

The hydroxyethyl cellulose, used as a 1 – 5 weight % aqueous solution, is used with the organic solvent solution of a copolymer consisting predominantly of an alkyl acrylate in an amount such that its solids content is 1 – 10% by weight, and preferably 3 – 7% by weight, of the total solids content.

As the liner having a flat, smooth surface that is used for applying the adhesive composition of this invention, the commercially available strippable paper can be used as such, but it is also possible to use the commercial stripping agent after applying same to a suitable support followed by drying.

While the thickness of the adhesive composition layer will be determined by the degree of breathability required for its intended use and the adhesive strength required, it is usually 10 –40 microns, and preferably 20 – 30 microns.

In applying the invention adhesive composition mixture, the conventional roll coater type coating machine is used.

As the substrate for use as the aforesaid backing, any will do so long as it is one having gas permeability. For instance, the perforated plastic films, cloths, nonwoven fabrics and papers can be used. Especially, in the case of the tapes and sheet materials for medical uses, the perforated polyethylene films and rayon nonwoven fabrics can be effectively used.

An adhesive coating which possesses excellent adhesiveness as well as permits the full breathing activity of the object adhered therewith can be obtained by the use of the invention adhesive composition. For instance, as mentioned in a hereinafter given Example, an adhesive composition incorporated with about 5% by weight of a hydroxyethyl cellulose has a moisture-transmission rate at a temperature of 37°C. and a relative humidity of 90 – 95% of 18.1 mg/cm$^2$-hr when the thickness of the adhesive coating is of the order of 25 microns (in the case where a backing having a moisture-transmission rate of 26.1 mg/cm$^2$-hr is used), thus achieving a moisture-transmission rate of more than four times that of the 4.3 mg/cm$^2$-hr of the case where the hydroxyethyl cellulose is not added. Hence, when the invention adhesive composition is used in preparing a surgical tape and the so prepared tape is adhered to the human body, it is very effective in preventing the irritating to the skin.

The following examples will be given for more fully illustrating the invention. The parts used in the examples are in all cases on a weight basis. The invention adhesive composition and the adhesive tape obtained by using the ordinary office stationery as backing and applying thereto the invention adhesive composition as the adhesive coating were submitted to the following performance and evaluated.

1. Cohesive strength of the adhesive composition.

The adhesive composition is applied to two sheets of glass, each 2.6 cm in width, 5 cm in length and 0.8 mm in thickness. After the adhesive composition had dried, the glass sheets are placed one on top of the other in such a manner that 1.3 cm of each the adhesive layers are laid in contact with each other. The sheets are then pressed together. The 0 degree pulling test is conducted using a bonded area of 3.4 cm$^2$. Further, the thickness of the adhesive layer is adjusted to 40 microns, and the shear strength at a pulling speed of 2 cm/min. is measured, this value being used as a measure of the cohesive strength.

2. Breathability of the adhesive tape.

A moisture-transmissible aluminum cup (moisture transmission area = 28.26 cm$^2$) satisfying the requirements of the JIS Method 6549 (Method for Testing the Moisture-transmissibility of Leather) is used, and measurements of the increase in weight are made at hourly intervals up to 5 hours in accordance with the procedure described in the foregoing JIS method. The amount of moisture transmission (mg) per square centimeter of moisture-transmission area per hour of moisture-transmission time (moisture-transmission rate mg/cm$^2$-hr) is then obtained from the slope of the measurements and used as a measure of the breathability. As the moisture absorbing agent, 20 grams of calcium chloride dihydrate is used, and the measurements are made under the conditions of a temperature of 37°C. and a relative humidity of 90 – 95%.

3. Adhesive strength of the adhesive tape.

An adhesive tape 1.0 cm in width having an adhesive coating of 25-micron thickness is prepared by the transfer method described in Example 1, using as the backing an office stationery. This adhesive tape is adhered to a stainless steel plate by application of a pressure of 1 kg/cm$^2$ for one minute. A 180-degree pulling test is then conducted with a pulling speed of 2 cm/min. to obtain the peeling strength (g/cm), which is used as a measure of the adhesive strength.

EXAMPLE 1 AND CONTROL 1

A reactor equipped with a reflux condenser and a stirrer was charged with 90 parts of 2-ethylhexyl acrylate, 7.4 parts of methyl methacrylate, 2.5 parts of methacrylic acid, 0.1 part of polyethylene glycol (degree of polymerization = 14) dimethacrylate, 0.2 part of benzoyl peroxide and 100 parts of ethyl acetate, and the polymerization reaction was carried out for 10 hours with gentle stirring. The polymerization conversion was 99.9%. 624 Parts of ethyl acetate was added to the resulting polymer solution, and an adhesive dope having a solids concentration of 13.8% (hereinafter designated dope A) was prepared.

41 Parts of a 1.8% aqueous solution of hydroxyethyl cellulose was than added to 100 parts of the foregoing dope A to prepare an adhesive composition dope whose hydroxyethyl cellulose content was 5% by weight of the total solids content (hereinafter designated dope B). When the cohesive strengths of dopes A and B were measured, there was no great difference. It was thus found that the cohesive strength does not drop by the addition of the hydroxyethyl cellulose.

This dope B was applied to a commercial strippable paper in an amount such that the thickness of the adhesive composition film, when dried, would become about 25 microns and dried for 30 minutes at a temperature of 93°C. At this stage, the adhesive composition is completely dry and is completely devoid of volatile components. Next, a commercial office stationary was overlaid stop this adhesive composition film and transferred and adhered thereto with the application of pressure. This was followed by again heat treating the adhesive composition film-adhered stationary for 30 minutes at 93°C. The strippable paper was then removed and an office stationary-backed adhesive tape was thus obtained. The transmission rate and adhesive strength of this adhesive tape was then measured.

As control, an adhesive tape prepared in like manner but using dope A not containing the hydroxyethyl cellulose was also measured for its transmission rate and adhesive strength. The results obtained in the cases of the adhesive composition containing the hydroxyethyl cellulose and that not containing the hydroxyethyl cellulose are shown together in Table 1.

Table 1

| | Dope used | Amount added of hydroethyl cellulose (wt %) | Cohesive strength (g/cm$^2$) | Thickness of adhesive coating ($\mu$) | moisture transmission rate (mg/cm$^2$-hr) | Adhesive strength (g/cm) |
|---|---|---|---|---|---|---|
| Example 1 | dope B | 5.0 | 2960 | 25.0 | 18.1 | 135 |
| Control 1 | dope A | 0 | 2640 | 24.3 | 4.3 | 190 |
| Commercial office Stationary | — | — | — | — | 26.1 | — |

Example 1 is the case where the adhesive composition containing the hydroxyethyl cellulose was used. The moisture-transmission rate demonstrated in this case was a very excellent one of 18.1 mg/cm$^2$-hr, which corresponds to about 70% of the moisture-transmission rate of the backing alone, i.e., the case where the office stationary is not applied the adhesive composition. On the other hand, in the case where dope A not containing the hydroxyethyl cellulose was used (Conrol 1), the moisture-transmission rate was only 4.3 mg/cm$^2$-hr, a value less than one-fourth of that of Example 1, in spite of the fact that the thickness of the adhesive coating was about the same.

While the adhesive strength of the adhesive tape of Example 1 is 135 g/cm, this is adequate for ordinary purposes.

EXAMPLE 2

An adhesive tape was prepared by uniformly applying the same dope B as that used in Example 1 to an office stationery of the same type as that used in Example 1, followed by drying for 30 minutes at a temperature of 93°C. The thickness of the adhesive coating of this adhesive tape was 25.5 microns, and its moisture-transmission rate was 16.2 mg/cm$^2$-hr. On the ohter hand, its adhesive strength was 130 g/cm.

It can be seen from this example that the method of preparing the adhesive tape has nothing to do with its moisture transmissibility, and that the adhesive composition dope is responsible for this property.

EXAMPLE 3

An adhesive tape in which the content of the hydroxyethyl cellulose in the adhesive composition was 10% by weight was prepared by operating exactly as in Example 1 but using 88 parts of a 1.7 weight % aqueous hydroxyethyl cellulose solution for each 100 parts of the same dope A as that used in Example 1. The so obtained adhesive tape had a 25.9-micro-thick adhesive coating, and its moisture-transmission rate was 16.4 mg/cm$^2$-hr, while its adhesive strength was 100 g/cm. Thus, the properties possessed by this adhesive tape were excellent.

EXAMPLE 4

An adhesive tape in which the content of the hydroxyethyl cellulose in the adhesive composition was 1.0 weight % was prepared by operating exactly as in Example 1 but using 15 parts of a 1.0 weight % aqueous hydroxyethyl cellulose solution for each 100 parts of the same dope A as that used in Example 1. The thickness of the adhesive coating of this adhesive tape was 25.0 microns, while the moisture-transmission rate and adhesive strength of this tape were 8.2 mg/cm$^2$-hr and 174 g/cm, respectively.

CONTROL 2

This experiment illustrates the case where the hydroxyethyl cellulose was used in excess of the range specified by this invention.

The experiment was carried out as in Example 1, except that 50 parts of a 4.8 weight % aqueous solution of the hydroxyethyl cellulose was used for each 100 parts of the same dope A as that used in Example 1 to prepared a commercial office stationary-backed adhesive tape in which the hydroxyethyl cellulose content in the adhesive composition was about 15% by weight. While the so obtained adhesive tape, whose thickness of the adhesive coating was 24.8 microns, had an excellent moisture-transmission rate of 17.2 mg/cm$^2$-hr, it was of no practical use, since its adhesive strength was too low, being only 70 g/cm.

CONTROL 3

Example 1 was repeated, except that 7 parts of a 1.0 weight % aqueous hydroxyethyl cellulose solution was used for each 100 parts of the same dope A as that used in Example 1 to prepare a commercial office stationary-backed adhesive tape in which the hydroxylethyl cellulose content in the adhesive composition was about 0.5% by weight. The thickness of the adhesive coating of the so obtained adhesive tape was 24.7 microns. On the other hand, while this adhesive tape had an excellent adhesive strength of 185 g/cm, its moisture-transmission rate was only 6.5 mg/cm$^2$-hr, and hence this tape could not possibly be called a breathable adhesive tape.

CONTROLS 4 - 17

These experiments illustrate that adhesive compositions having an adequate moisture transmissiblity cannot be obtained even though water-soluble or hydrophilic polymers other than hydroxyethyl cellulose are added to the copolymer consisting predominantly of alkyl acrylates.

Various water-soluble or hydrophilic polymers were mixed with the same dope A as that used in Example 1, the water-soluble ones being used as aqueous solution and the water-insoluble ones being used as organic solvent solutions. Then by operating as in Example 1 adhesive tapes having a commercial office stationary as backing were prepared. Further, adhesive tapes having adhesive coatings of varied thickness were prepared as in Control 1.

These tapes were measured for their adhesive coating thickness and moisture-transmission rate, with the results shown in Table 2.

permeability over the cases where no additive was added (Controls 14 - 17). Hence, none of these compositions could possibly be considered as being a breathable adhesive composition.

EXAMPLES 5 - 8

Adhesive compositions of varied compositions were prepared by operating as in Example 1 but varying the classes and amounts of the monomers used. The results obtained are shown in Table 3. In all instances the amount of the hydroxyethyl cellulose was 5% by weight of the total solids content. As is apparent from Table 3, the compositions of Examples 5 - 8 demonstrated in all cases satisfactory moisture-transmission rate as well as adhesive strength.

Table 3

|  | Copolymer composition | | | | Thickness of adhesive coating ($\mu$) | Moisture transmission rate (mg/cm$^2$-hr) | Adhesive strength (g/cm) |
| --- | --- | --- | --- | --- | --- | --- | --- |
|  | 2-Ethylhexyl acrylate (parts) | Vinyl acetate (parts) | Methacrylic acid (parts) | Polyethylene glycol dimethacrylate (part) | | | |
| Example 5 | 90.0 | 7.5 | 2.5 | 0.05 | 20.7 | 14.7 | 177 |
| Example 6 | 97.5 | — | 2.5 | 0.05 | 19.5 | 16.4 | 180 |
| Example 7 | 75.0 | 25.0 | — | — | 22.2 | 13.1 | 204 |
| Example 8 | 95.0 | — | 5.0 | — | 23.6 | 14.8 | 280 |

We claim:
1. A breathable adhesive tape or drape having a gas- and moisture-transmissible adhesive layer adhered to a gas- and moisture-transmisible sheetlike substrate, said adhesive layer comprising, of the total composition of 100 parts by weight, 90 – 99 parts by weight of a tacky copolymer obtained by copolymerizing
   a. 75 – 95 mol% of at least one alkyl acrylate, the alkyl group of which contains 1 to 14 carbon atoms and the average number of which carbon atoms is 4 to 12, or a mixture of at least one class of said alkyl acrylate with methyl methacrylate and/or vinyl acetate in a molar ratio of 5 or more to 1; with

Table 2

|  |  | Additive | | | Thickness of adhesive coating ($\mu$) | Moisture permeature speed (mg/cm$^2$-hr) |
| --- | --- | --- | --- | --- | --- | --- |
|  |  | Class | wt% | Solvent | | |
| Control | 4 | cellulose acetate | 10.0 | Acetone | 29.0 | 4.1 |
| " | 5 | methyl cellulose | 15.0 | Water | 21.0 | 6.7 |
| " | 6 | ethyl cellulose | 15.0 | Acetone | 21.0 | 5.0 |
| " | 7 | hydroxypropyl cellulose | 10.0 | Water | 30.1 | 5.3 |
| " | 8 | carboxymethyl cellulose | 15.0 | Water | 20.3 | 7.5 |
| " | 9 | cellulose acetate terephthalate | 10.0 | Acetone | 30.6 | 3.5 |
| " | 10 | polyethylene glycol | 10.0 | Methylene chloride | 28.9 | 4.5 |
| " | 11 | polyvinyl pyrolidone | 15.0 | Water | 22.1 | 6.9 |
| " | 12 | sodium polyacrylate | 15.0 | Water | 22.6 | 4.8 |
| " | 13 | polyacrylamide | 10.0 | Water | 26.2 | 4.8 |
| " | 14 | — | — | — | 14.2 | 7.0 |
| " | 15 | — | — | — | 24.3 | 4.3 |
| " | 16 | — | — | — | 27.5 | 3.5 |
| " | 17 | — | — | — | 40.9 | 2.8 |

While Controls 4 – 13 were in all cases those in which either a water-soluble or hydrophilic polymer was used instead of the hydroxyethyl cellulose, in no case was there observed a marked improvement in moisture b. 5 – 25 mol% of acrylic acid and/or methacrylic acid, and 10 – 1 parts by weight of a hydroxyethyl cellulose.

2. The article of claim 1 wherein said copolymer is that obtained by copolymerizing
   a. 94 – 98 mol% of at least one alkyl acrylate, the alkyl group of which contains 1 to 14 carbon atoms and the average number of which carbon atoms is 4 to 12, or a mixture of at least one class of said alkyl acrylate with a member selected from the group consisting of methyl methacrylate, vinyl acetate and mixtures thereof in a molar ratio of 5 or more to 1;
   b. 2 – 6 mol% of a member selected from the group consisting of acrylic acid, methacrylic acid and a mixture thereof; and
   c. 0.002 – 0.05 mol% of a compound selected from the group consisting of diallyl phthalate, enthylene glycol dimethacrylate, polyethylene glycol dimethacrylate, trimethylolethane trimethacrylate and pentaerythritol tetra methacrylate.

* * * * *

UNITED STATES PATENT AND TRADEMARK OFFICE
CERTIFICATE OF CORRECTION

PATENT NO. : 3,975,570
DATED : August 17, 1976
INVENTOR(S) : ONO, ET AL.

It is certified that error appears in the above-identified patent and that said Letters Patent are hereby corrected as shown below:

Claim 2, subparagraph "c.", line 2, delete "enthylene", insert -- ethylene --

Signed and Sealed this

Eighteenth Day of October 1977

[SEAL]

Attest:

RUTH C. MASON
*Attesting Officer*

LUTRELLE F. PARKER
*Acting Commissioner of Patents and Trademarks*